United States Patent [19]

Ziemann et al.

[11] Patent Number: 4,661,640

[45] Date of Patent: Apr. 28, 1987

[54] SUBSTITUTED 5-CYCLOALKYL-2,2-DI-METHYL-PENTAN-3-ONES

[75] Inventors: Heinz Ziemann, Leichlingen; Karl-Heinrich Mohrmann, Wuppertal, both of Fed. Rep. of Germany

[73] Assignee: Bayer Aktiengesellschaft, Leverkusen, Fed. Rep. of Germany

[21] Appl. No.: 833,316

[22] Filed: Feb. 24, 1986

Related U.S. Application Data

[62] Division of Ser. No. 676,136, Nov. 29, 1984, Pat. No. 4,602,115.

[30] Foreign Application Priority Data

Dec. 1, 1983 [DE] Fed. Rep. of Germany ....... 3343532

[51] Int. Cl.$^4$ ........................................... C07C 49/233
[52] U.S. Cl. ................................... 568/308; 568/375; 568/376; 568/377; 568/380
[58] Field of Search ............... 568/308, 375, 376, 377, 568/380

[56] References Cited

U.S. PATENT DOCUMENTS

| | | | |
|---|---|---|---|
| 2,440,669 | 4/1948 | Thurston | 568/308 |
| 3,458,569 | 7/1969 | Bicking et al. | 568/308 |
| 4,347,192 | 8/1982 | Mueller | 568/308 |
| 4,380,628 | 4/1983 | Elbe et al. | 548/341 |

Primary Examiner—James H. Reamer
Attorney, Agent, or Firm—Sprung Horn Kramer & Woods

[57] ABSTRACT

Novel substituted 5-cycloalkyl-2,2-dimethyl-pentan-3-ones of the formula

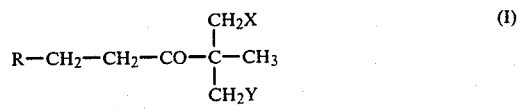

(I)

in which
R is optionally substituted cycloalkyl,
X is halogen and
Y is hydrogen or halogen, The new compounds are valuable intermediates for the synthesis of substances having plant growth-regulating and fungicidal properties.

4 Claims, No Drawings

SUBSTITUTED 5-CYCLOALKYL-2,2-DI-METHYL-PENTAN-3-ONES

This is a division of application Ser. No. 676,136, filed Nov. 29, 1984 now U.S. Pat. No. 4,602,115.

The present invention relates to new substituted 5-cycloalkyl-2,2-dimethyl-pentan-3-ones. The novel compounds are valuable intermediates for the synthesis of substances having plant growth-regulating and fungicidal activity.

It has already been disclosed that azolyl-methylketones can be used as intermediates for the preparation of azolyl derivatives having plant growth-regulating and fungicidal properties (compare European Patent Specification No. 0,032,200 and European Patent Specification No. 0,031,911). Thus, for example, 1-cyclohexyl-2-(1,2,4-triazol-1-yl)-4,4-bis-fluoromethyl-pentan-3-one can be synthesized by reacting 1-(1,2,4-triazol-1-yl)-3,3-bis-fluoromethyl-butan-2-one with cyclohexyl-methyl bromide according to the following equation:

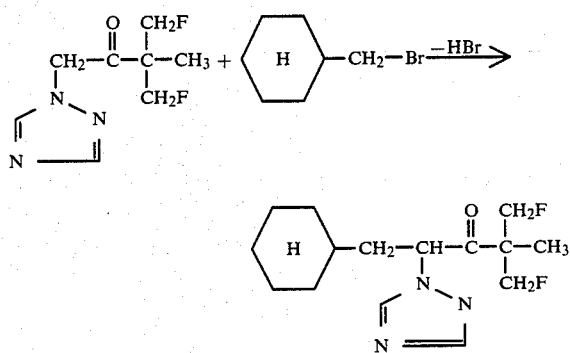

The disadvantage is, however, that in this type of preparation of azolyl derivatives having a plant growth-regulating and fungicidal activity, the azolyl-methylketones required as intermediates can be obtained only by multi-stage syntheses, and some of the materials thereby employed as starting substances are accessible only with difficulty.

The present invention now provides, as new compounds, the substituted 5-cycloalkyl-2,2-dimethyl-pentan-3-ones of the formula

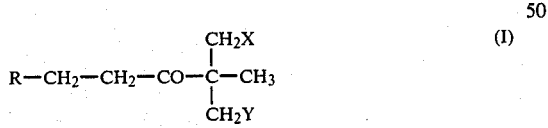

in which
R represents optionally substituted cycloalkyl,
X represents halogen and
Y represents hydrogen or halogen.

The new substances of the formula (I) are obtained by a process, which comprises reacting selectively a ketone of the formula

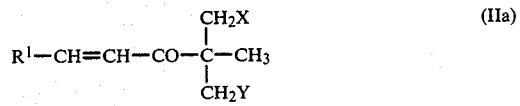

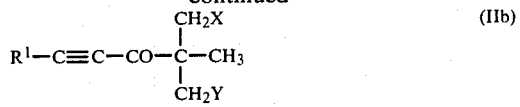

or

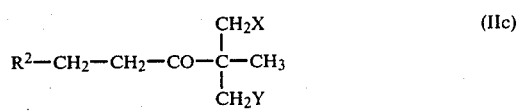

in which
X and Y have the abovementioned meanings,
R¹ represents optionally substituted cycloalkyl, optionally substituted cycloalkenyl or optionally substituted aryl and
R² represents optionally substituted aryl,
with hydrogen in the presence of a hydrogenation catalyst and, if appropriate, in the presence of a diluent.

It has also been found that the new substituted 5-cycloalkyl-2,2-dimethyl-pentan-3-ones of the formula (II) are particularly suitable as intermediates for the preparation of 4-azolyl-5-cycloalkyl-2,2-dimethyl-pentan-3-ones and -ols having a plant growth-regulating and fungicidal activity.

Surprisingly, 4-azolyl-5-cycloalkyl-2,2-dimethyl-pentan-3-ones and -ols having a plant growth-regulating and fungicidal action can be prepared from the substituted 5-cycloalkyl-2,2-dimethyl-pentan-3-ones of the formula (I) according to the invention more simply and in a higher yield than by the process known hitherto, in which the corresponding 4-azolyl-2,2-dimethyl-butan-3-ones have been used as intermediates.

Formula (I) provides a general definition of the substances according to the invention. Preferably, in this formula,
R represents cycloalkyl which has 5 to 7 carbon atoms and is optionally mono-, di- or tri-substituted by identical or different alkyl radicals with 1 or 3 carbon atoms,
X represents fluorine or chlorine and
Y represents hydrogen, fluorine and chlorine.

Particularly preferred compounds of the formula (I) are those in which
R represents cyclohexyl which is optionally substituted by methyl;
X represents fluorine and
Y represents hydrogen or fluorine.

If, for example, 2,2-bisufluoromethyl-5-phenyl-pent-4-en-3-one and hydrogen are used as the starting substances and palladium and ruthenium-on-active charcoal are used as catalysts, the course of the reaction in the process according to the invention can be represented by the following equation:

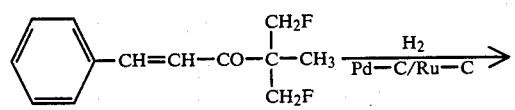

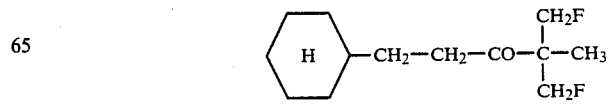

If, for example, 2,2-bisfluoromethyl-5-(cyclohexen-1-yl)-pent-4-in-3-one and hydrogen are used as starting substances and Raney nickel is used as the catalyst, the course of the reaction in the process according to the invention can be represented by the following equation:

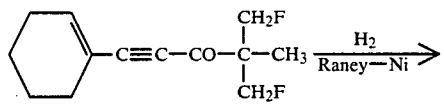

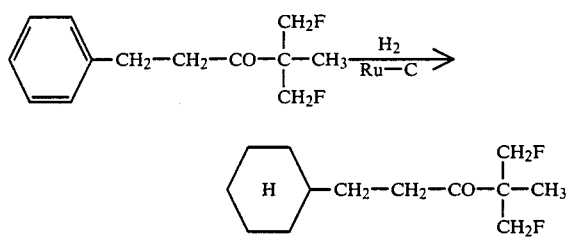

If, for example, 2,2-bisfluoromethyl-5-phenyl-pentan-5-one and hydrogen are used as starting substances and ruthenium-on-active charcoal is used as the catalyst, the course of the reaction in the process according to the invention can be represented by the following equation:

The formulae (IIa), (IIb) and (IIc) provide general definitions of the ketones to be used as starting substances for carrying out the process according to the invention. In these formulae, $R^1$ preferably represents cycloalkyl with 5 to 7 carbon atoms, cycloalkenyl with 5 to 7 carbon atoms or phenyl, in each case optionally mono-, di- or tri-substituted by identical or different alkyl radicals with 1 to 3 carbon atoms. $R^2$ preferably represents phenyl which is optionally mono-, di- or tri-substituted by identical or different alkyl radicals with 1 to 3 carbon atoms.

The ketones of the formula (IIa) are not yet known. Thus, the present invention also provides, as new compounds, the ketones of the formula (IIa).

The ketones of the formula (IIa) are obtained by a process, which comprises reacting a butan-2-one of the formula

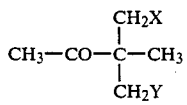  (III)

in which

X and Y have the abovementioned meanings, with an aldehyde of the formula

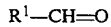  (IV)

in which $R^1$ has the abovementioned meanings, in the presence of a diluent, such as, for example, an alcohol, and in the presence of a base, such as, for example, an alkali metal hydroxide or carbonate, at temperatures between 10° C. and 80° C.

The butan-2-ones of the formula (III) and the aldehydes of the formula (IV) are known compounds of organic chemistry.

Further, the ketones of the formula (IIb) are not yet known. Said ketones of the formula (IIb) are the subject matter of a separate copending patent application.

The ketones of the formula (IIb) are obtained by a process, which comprises reacting an acetylene derivative of the formula

  (V)

in which $R^1$ has the abovementioned meanings, with a pivalic acid halide of the formula

  (VI)

in which

X and Y have the abovementioned meanings and

Hal represents halogen, preferably chlorine or bromine, in the presence of Cu-(I)-ions as the catalyst, and in the presence of a diluent, such as, for example, toluene or pyridine, and in the presence of a base, such as, for example, triethylamine, at temperatures between 20° C. and 100° C.

The acetylene derivatives of the formula (V) and the pivalic acid halides of the formula (VI) are known compounds of organic chemistry.

The ketones of the formula (IIc) are also not yet known. Thus, the present invention also provides, as new compounds, the ketones of the formula (IIc).

The ketones of the formula (IIc) are obtained by a process, which comprises selectively hydrogenating the double bond or triple bond of a ketone of the formula

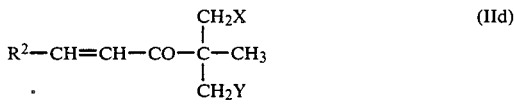  (IId)

or

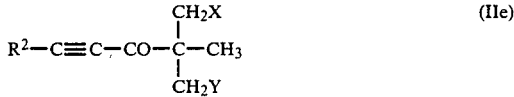  (IIe)

in which $R^2$, X and Y have the abovementioned meanings, with hydrogen in the presence of a diluent, such as, for example, methanol, and in the presence of a catalyst, such as, for example, Raney nickel or palladium-on-charcoal, under normal pressure or under increased pressure, such as, preferably, 30 to 40 bar, at temperatures between 20° C. and 40° C.

The process according to the invention is carried out in the liquid phase, preferably in the presence of diluents, using a suspended, pulverulent hydrogenation catalyst. The hydrogenation according to the invention can be carried out discontinuously (batchwise) or continuously as liquid phase or trickle phase hydrogenation in known hydrogenation reactors, such as autoclaves, autoclave cascades, tube reactors or circulatory reactors. The preferred procedure is discontinuous liquid phase hydrogenation in an autoclave under increased pressure.

Possible diluents in carrying out the process according to the invention are inert organic solvents. These include, preferably, alcohols, such as methanol, ethanol, isopropanol or ethylene glycol; ethers, such as diethyl ether, diisopropyl ether, ethylene glycol monomethyl ether, ethylene glycol dimethyl ether, dioxane or tetrahydrofuran; saturated hydrocarbons, such as n-heptane or cyclohexane; and esters, such as ethyl acetate.

Examples of suitable hydrogenation catalysts for the process according to the invention are those which consist of or contain metals and/or compounds of subgroup 8 of the Mendeleev periodic table of the elements. The metals ruthenium, rhodium, palladium, platinum, cobalt and nickel and compounds thereof are preferred here. The metal compounds can be, for example, oxides, hydroxides and/or hydrated oxides. In addition, the metals copper, vanadium, molybdenum, chromium and/or manganese and compounds of these metals can be present.

The hydrogenation catalysts can consist exclusively or predominantly of substances which transfer hydrogen, but these can also be applied to supports.

Examples of possible supports for the substances which transfer hydrogen are: inorganic materials, such as kieselguhr, salicic acid, aluminium oxide, alkali metal and alkaline earth metal silicates, aluminium silicates, montmorillonite, zeolites, spinels, dolomite, kaolin, magnesium silicates, zirconium oxide, zinc oxide, calcium carbonate, silicon carbide, aluminium phosphate, boron phosphate, asbestos, active charcoal or barium sulphate, and also organic materials, for example naturally occurring or synthetic compounds with high molecular weights, such as silk, polyamides, polystyrenes, cellulose or polyurethanes. Inorganic supports in powder form are preferred.

Such supported catalysts can in general contain 0.5 to 50% by weight, or preferably 1 to 10% by weight, of the substance which transfers hydrogen, based on the total weight of the supported catalyst. The substance which transfers hydrogen can thereby be homogeneously distributed in the support, but catalysts containing a deposit of the substance which transfers hydrogen in their outer layer or on their surface are preferred. The catalysts which can be used in the process according to the invention can be prepared and shaped in a known manner (see, for example, Houben-Weyl, Methoden der organischen Chemie (Methods of Organic Chemistry), Volume 4, Ic, Part I, pages 16 to 26, Georg Thieme Verlag, Stuttgart, 1980).

Preferred supported catalysts are ruthenium-on-charcoal, ruthenium-on-aluminium oxide, rhodium-on-charcoal, rhodium-on-aluminium oxide, palladium-on-charcoal, palladium-on-aluminium oxide, palladium-on-calcium carbonate, palladium-on-barium sulphate, palladium-on-salicic acid, platinum-on-charcoal and platinum-on-aluminium oxide, nickel-on-kieselguhr, nickel-on-aluminium oxide and nickel and palladium-on-aluminium oxide.

Examples of preferred hydrogenation catalysts which consist exclusively or predominantly of the substance which transfers hydrogen are oxidic catalysts, such as palladium oxide, platinum oxide, ruthenium oxide and/or rhodium oxide/platinum according to Nishimura, and furthermore black catalysts which can be prepared by production of corresponding metal salts or metal salt mixtures with alkali metal hydrides, alkali metal boronates, metal-alkyls, hydrazine, formaldehyde, hydrogen or more electropositive metals, such as palladium black, platinum black and rhodium black; and skeleton catalysts of the Raney type, such as Raney nickel, Raney cobalt, Raney nickel/cobalt, Raney nickel/iron, Raney nickel/copper, Raney nickel/iron/chromium, Raney nickel/palladium and Raney nickel/iron/vanadium.

The selection of one or more of the hydrogenation catalysts mentioned advantageously depends on the structure of the starting ketones of the formulae (IIa), (IIb) and (IIc) to be hydrogenated according to the invention.

If the ketones of the formulae (IIa) and (IIb) contain optionally substituted cycloalkenyl radicals or optionally substituted cycloalkyl radicals as the substituent $R^1$, those catalysts which contain or consist of nickel and/or palladium are particularly preferred for conversion thereof into saturated ketones of the formula (I).

If the ketones of the formulae (IIa) and (IIb) contain optionally substituted aryl radicals as the substituent $R^1$ or if a ketone of the formula (IIc) is concerned, those catalysts which contain or consist of ruthenium, rhodium and/or platinum are particularly preferred for conversion thereof into saturated ketones of the formula (I).

The hydrogenation catalysts are used in the process according to the invention in an amount such that 0.05 to 2.5% by weight, preferably 0.1 to 1% by weight, of the substance which transfers hydrogen is present, based on the metal weight of the reaction mixture.

Mixtures of two or more of the hydrogenation catalysts mentioned can also be used for carrying out the process according to the invention.

The catalytic activity of the hydrogenation catalysts is in general substantially retained in carrying out the process according to the invention, so that these can be used repeatedly in the case of a discontinuous procedure, and can remain in use for a relatively long time in the case of the continuous procedure.

The reaction temperatures can be varied within a substantial range. In general, the reaction is carried out in the range between 0° C. and 150° C., preferably between 20° C. and 120° C. Reaction temperatures in the range from 20° C. to 60° C. are particularly preferred for the hydrogenation of aliphatic and/or cycloaliphatic C—C multiple bonds in the ketones of the formulae (IIa) and (IIb) with the catalysts preferred for this hydrogenation, whilst temperatures in the range from 60° C. to 120° C. are particularly preferred for the hydrogenation of aryl radicals in the ketones of the formulae (IIa), (IIb) and (IIc) with the catalysts preferred for this hydrogenation.

The hydrogenation reactions according to the invention are preferably carried out under increased pressure. In general, the hydrogenation is carried out between 1 and 150 bar, preferably under 20 to 120 bar. Pressures in the range from 5 to 50 bar are particularly preferred for the hydrogenation of aliphatic and/or cycloaliphatic C—C multiple bonds in the ketones of the formulae (IIa) and (IIb) with the catalysts preferred for this hydrogenation, whilst pressures in the range from 5 to 120 bar are particularly preferred for the hydrogenation of aryl radicals in the ketones of the formulae (IIa), (IIb) and (IIc) with the catalysts preferred for this hydrogenation.

The reaction time required for the process according to the invention depends on the reaction temperature, the partial pressure of hydrogen, the intensity of mixing of the reaction mixture and the activity and concentration of the hydrogenation catalyst. In general, the reaction time necessary is in the range from 15 minutes to several hours.

In the simplest embodiment, the process according to the invention can be carried out, for example, discontinuously in the following manner: an autoclave which can be temperature-controlled and is provided with a stirring or mixing device is charged in a suitable manner with a ketone of the formula (IIa), (IIb) or (IIc), the hydrogenation catalyst and the diluent. After the air has been removed from the autoclave and hydrogen has been forced in up to the desired pressure, the mixture is heated to the chosen reaction temperature, with intensive mixing. The course of the reaction can easily be monitored by measuring the hydrogen consumption, which is compensated by feeding in further hydrogen. The hydrogenation has ended when no further hydrogen is consumed and the amount of hydrogen consumed approximately corresponds to the theoretically required amount of hydrogen.

When the hydrogenation has ended, the reaction mixture is cooled, let down, and worked up in a known manner, for example by removing the catalyst by filtration and distilling off the diluent.

In a particular embodiment of the reaction according to the invention, a procedure is followed in which ketones of the formula (IIa) which carry an optionally substituted aryl radical as the substituent $R^1$ are hydrogenated to the corresponding ketones of the formula (IIc) in a first stage, and these ketones are then hydrogenated to the end products of the formula (I) in a second stage (compare also the preparation examples). It should be emphasised that only the C—C multiple bonds are hydrogenated, with a high selectivity, whilst the CO double bond is retained.

As already mentioned, the new 5-cycloalkyl-2,2-dimethyl-pentan-3-ones of the formula (I) are useful intermediates for the synthesis of 4-azolyl-5-cycloalkyl-2,2-dimethyl-pentan-3-ones and -ols having fungicidal and plant growth-regulating properties.

Such 4-azolyl-5-cycloalkyl-2,2-dimethyl-pentan-3-ones and -ols of the formula (VII)

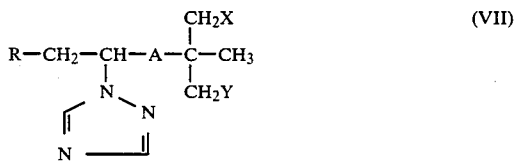

in which
R, X and Y have the abovementioned meanings and
A represents a keto group or the CH(OH) group,
can be prepared by a process in which 5-cycloalkyl-2,2-dimethyl-pentan-3-ones of the formula (I)

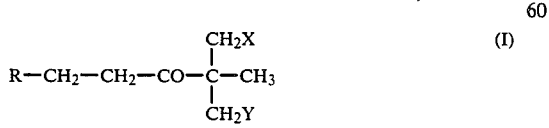

in which
R, X and Y have the abovementioned meanings, are reacted with chlorine or bromine in the presence of an inert organic solvent, such as, for example, ether or chlorinated or non-chlorinated hydrocarbons, at room temperature, or are reacted with customary chlorinating agents, such as, for example, sulphuryl chloride, at 20° C. to 60° C.; the halogenoketones thus obtained, of the formula (VIII)

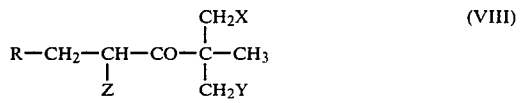

in which
R, X and Y have the abovementioned meanings and
Z represents chlorine or bromine,
are then reacted with 1,2,4-triazole in the presence of an inert organic solvent, such as, for example, acetonitrile, and in the presence of an acid-binding agent, such as, for example, potassium carbonate, or in the presence of an excess of 1,2,4-triazole, at temperatures between 60° C. and 120° C.; and, if appropriate, the 4-azolyl-5-cycloalkyl-2,2-dimethyl-pentan-3-ones thus obtained, of the formula (VIIa)

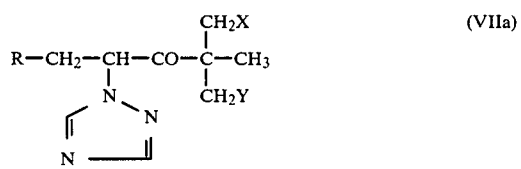

in which
R, X and Y have the abovementioned meanings,
are subsequently reduced by reaction with complex hydrides, such as sodium borohydride or lithium alanate, in the presence of a polar organic solvent, such as, for example, an alcohol, at temperatures between 0° C.; or are reduced by reaction which aluminium isopropylate in the presence of a diluent, such as, for example, isopropanol, at temperatures from 20° C. to 120° C.

The 4-azolyl-5-cycloalkyl-2,2-dimethyl-pentan-3-ones and -ols of the formula (VII) have powerful fungicidal and plant growth-regulating properties (compare European Patent No. 0,031,911 and European Patent No. 0,032,200).

The preparation and use of the substances according to the invention can be seen from the following examples.

PREPARATION EXAMPLES

Example 1

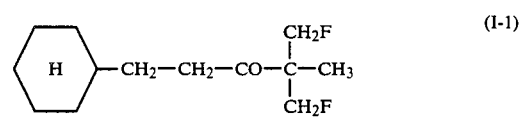

Process variant 1

1st stage:

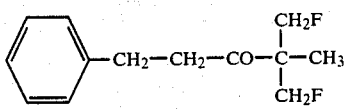 (II-1)

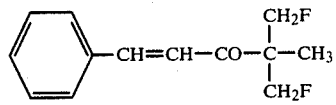 (II-2)

A 120 liter stainless steel stirred autoclave which can be temperature-controlled with the aid of an adjustable thermostat was charged with 30 kg (133.9 mol) of 2,2-bisfluoromethyl-5-phenyl-pent-4-en-3-one, 60 liters of methanol and 0.6 kg of Raney nickel.

After the autoclave had been closed and the air had been displaced with nitrogen the mixture employed was charged with hydrogen up to a pressure of 30 bar and was then heated to 80° C., with stirring. As soon as this temperature had been reached, the hydrogen pressure was increased to 40 bar and was maintained at this level in accordance with the rate of consumption of the hydrogen throughout the entire reaction time.

When the uptake of hydrogen had ended, after about 5 hours, stirring was continued under the abovementioned hydrogenation conditions for a further hour in order to bring the reaction to completion, and the mixture was then cooled to room temperature and let down to normal pressure.

The product solution separated off from the catalyst by filtration was further reacted directly in the second stage without being isolated. The resulting 2,2-bisfluoromethyl-5-phenyl-pentan-3-one had a content of 98% (determined by gas chromatography).

2nd stage:

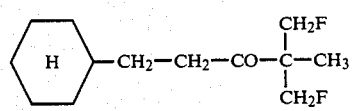 (I-1)

A 120 liter stainless steel stirred autoclave which can be temperature-controlled with the aid of an adjustable thermostat was charged with a solution of 29.7 kg (131.4 mol) of 2,2-bisfluoromethyl-5-phenyl-pentan-3-one in 60 liters of methanol and 0.72 kg of a catalyst containing 5% of ruthenium-on-active charcoal.

After the autoclave had been closed and the air had been displaced with nitrogen, the mixture employed was charged with hydrogen up to a pressure of 50 bar and was heated to 90° C., with stirring. As soon as this temperature had been reached, the hydrogen pressure was increased to 100 bar and was maintained at this level in accordance with the rate of consumption of the hydrogen throughout the entire reaction time.

When the uptake of hydrogen had ended, after about 6 hours, stirring was continued under the abovementioned hydrogenation conditions for a further hour in order to bring the reaction to completion, and the mixture was then cooled to room temperature and let down to normal pressure.

The production solution separated off from the catalyst by filtration was freed from the methanol in a rotary evaporator.

30.3 kg (99.4% of theory) of 2,2-bisfluoromethyl-5-cyclohexyl-pentan-3-one were obtained as an oil with a content of 96% (determined by gas chromatography).

Preparation of the starting substance:

A mixture of 106.1 g (1 mol) of benzaldehyde, 136.1 g (1 mol) of 3,3-bisfluoromethyl-butan-2-one, 300 g of methanol and 40 g (1 mol) of sodium hydroxide in 70 g of water was stirred at room temperature for 3 hours. The crystalline product was then filtered off and dried.

201.8 g (90% of theory) of 2,2-bisfluoromethyl-5-phenyl-pent-4-en-3-one of melting point 45° C. were obtained.

Example 2

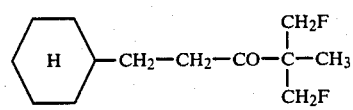 (I-1)

Process variant 2

A 0.7 liter stainless steel stirred autoclave which can be temperature-controlled with the aid of an adjustable thermostat was charged with 112 g (0.5 mol) of 2,2-bisfluoromethyl-5-phenyl-pent-4-en-3-one, 300 ml of methanol, 2,8 g of a catalyst containing 5% of palladium-on-active charcoal and 2.8 g of a catalyst containing 5% of ruthenium-on-active charcoal.

After the autoclave had been closed and the air had been displaced by nitrogen, hydrogen was passed in up to a pressure of 30 bar and the mixture was heated to 40° C., with stirring. As soon as this temperature was reached, the hydrogen pressure was increased to 50 bar and was maintained at this level until the uptake of hydrogen subsided ($H_2$ consumption about 0.5 mol in 1.5 hours). The reaction solution was then increased to 70° C. and the hydrogen pressure was increased to 100 bar, and the hydrogenation was continued under these conditions by continuously forcing more hydrogen up to a pressure of 100 bar in accordance with the hydrogen consumption, which can be recognised by the drop in pressure ($H_2$ consumption about 1.5 mol in 5 hours).

When the uptake of hydrogen had ended, the mixture was cooled to room temperature and let down to normal pressure. The product solution separated off from the catalyst by filtration was freed from the methanol in a rotary evaporator.

113 g (97.4% of theory) of 2,2-bisfluoromethyl-5-cyclohexyl-pentan-3-one were obtained as an oil with a content of 89% (determined by gas chromatography).

Example 3

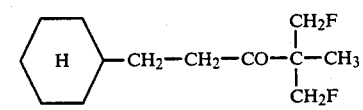 (I-1)

Process variant 3

1st stage:

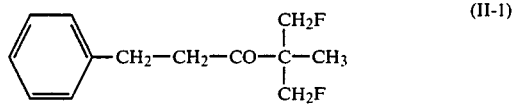

(II-1)

A 0.3 liter stainless steel stirred autoclave which can be temperature-controlled with the aid of an adjustable thermostat was charged with 44.4 g (0.2 mol) of 2,2-bis-fluoromethyl-5-phenyl-pent-4-in-3-one, 170 ml of methanol and 5 g of Raney nickel.

After the autoclave had been closed and the air had been displaced with hydrogen, the mixture employed was charged with hydrogen up to a pressure of 30 bar and was heated to 30° C., with stirring. As soon as this temperature had been reached, the hydrogen pressure was increased to 50 bar and was maintained at this level in accordance with the rate of consumption of the hydrogen throughout the entire reaction time.

When the uptake of hydrogen had ended, after about 2 hours, stirring was continued under the abovementioned hydrogenation conditions for a further hour in order to bring the reaction to completion, and the mixture was then cooled to room temperature and let down to normal presssure.

The product solution separated from the catalyst by filtration was freed from the methanol in a rotary evaporator.

44.5 g (98.5% of theory) of 2,2-bisfluoromethyl-5-phenyl-pentan-3-one were obtained as an oil with a content of 96.5% (determined by gas chromatography).
2nd stage:

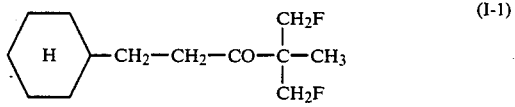

(I-1)

The reaction proceeds in the same way as the 2nd stage of process variant 1.
Preparation of the starting substance

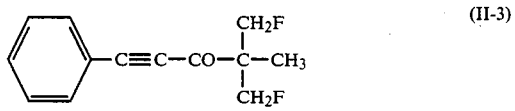

(II-3)

10.1 g (0.1 mol) of triethylamine and 1.43 g (0.01 mol) of copper-I bromide were initially introduced into 30 ml of pyridine, under nitrogen. 10.2 g (0.1 mol) of phenylacetylene were added and the mixture was subsequently stirred for 30 minutes. Thereafter, 15.6 g (0.1 mol) of α,α-bisfluoromethyl-propionyl chloride were added dropwise to the reaction mixture, the temperature thereby being kept at 60° C. The mixture was stirred at this temperature for 15 hours, cooled, washed with water, dried over sodium sulphate and concentrated in vacuo. The residue was purified by distillation.

17.3 g (78% of theory) of 2,2-bisfluoromethyl-5-phenyl-pent-4-in-3-one of boiling point 103° C. to 105° C./0.2 mbar were obtained.

Example 4

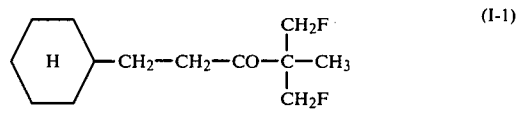

(I-1)

Process variant 4

A 0.3 liter stainless steel stirred autoclave which can be temperature-controlled with the aid of an adjustable thermostat was charged with 24 g (0.106 mol) of 2,2-bis-fluoromethyl-5-(cyclohexen-1-yl)-pent-4-in-3-one, 120 ml of methanol and 5 g of Raney nickel.

After the autoclave had been closed and the air had been displaced with nitrogen, the mixture employed was charged with hydrogen up to a pressure of 50 bar and was heated to 50° C., with stirring. As soon as this temperature had been reached, the hydrogen pressure was increased to 70 bar and was kept at this level in accordance with the rate of consumption of the hydrogen throughout the entire reaction time.

When the uptake of hydrogen had ended, stirring was continued under the abovementioned hydrogenation conditions for a further hour in order to bring the reaction to completion, and the mixture was then cooled to room temperature and let down to normal pressure.

The product solution separated off from the catalyst by filtration was freed from the methanol on a rotary evaporator.

23.5 g (95.5% of theory) of 2,2-bisfluoromethyl-5-cyclohexyl-pentan-3-one were obtained as an oil with a content of 88.5% (determined by gas chromatography).
Preparation of the starting substance

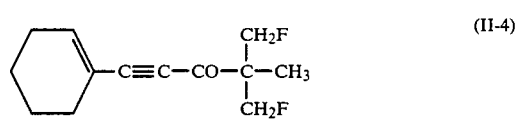

(II-4)

10.1 g (0.1 mol) of triethylamine and 1.43 g (0.1 mol) of copper I bromide were initially introduced into 30 ml of pyridine under nitrogen. 10.6 1 g (0.1 mol) of cyclohexen-1-yl-acetylene were added and the mixture was subsequently stirred for 30 minutes. Thereafter, 15.6 g (0.1 mol) of α,α-bis-fluoromethyl-pripionyl chloride were added dropwise to the reaction mixture and the temperature was kept at 70° C. The mixture was subsequently stirred at this temperature for 15 hours, cooled, washed with water, dried over sodium sulphate and concentrated in vacuo. The residue was purified by distillation.

18.1 g (80% of theory) of 2,2-bisfluoromethyl-5-(cyclohexen-1-yl)-pent-4-in-3-one of boiling point 106° C. to 109° C./0.3 mbar were obtained.

Preparation of 4-azolyl-5-cycloalkyl-2,2-dimethyl-pentan-3-ones of the formula (VII)

Example 5

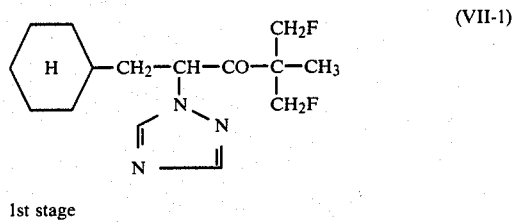

1st stage

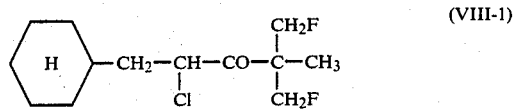

232.3 g (1 mol) of 2,2-bisfluoromethyl-5-cyclohexyl-pentan-3-one (Example 1) were heated to 80° C. and 161.9 g (1.2 mol) of sulphuryl chloride were added dropwise in the course of 1 hour. The mixture was subsequently stirred at 80° C. for 5 hours and excess sulphuryl chloride was then distilled off in vacuo. After the mixture had been cooled to 20° C., 500 ml of methyl isobutyl ketone were added. The organic solution was washed neutral with water, dried over magnesium sulphate and concentrated in vacuo. The residue was distilled.

252 g (90% of theory) of 2,2-bisfluoromethyl-5-chloro-5-cyclohexyl-pentan-3-one of boiling point 118° C. to 120° C./2.5 mbar were obtained.

2nd stage:

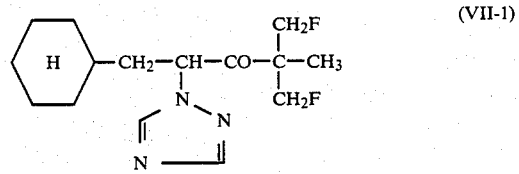

266.7 g (1 mol) of 2,2-bisfluoromethyl-4-chloro-5-cyclohexyl-pentan-3-one, 69.1 g (1 mol) of 1,2,4-triazole and 165.8 g (1.2 mol) of potassium carbonate in 1000 ml of methyl isobutyl ketone were heated under reflux for 6 hours. After cooling, the mixture was washed with dilute hydrochloric acid and washed neutral with water. The organic phase was dried over magnesium sulphate and concentrated in vacuo.

329 g (88% of theory) of 2,2-bisfluoromethyl-5-cyclohexyl-4-(1,2,4-triazol-1-yl)-pentan-3-one of refractive index $n_D^{20}=1.4933$ were obtained.

Example 6

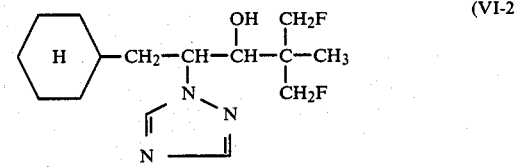

299 g (1 mol) of 2,2-bisfluoromethyl-5-cyclohexyl-4-(1,2,4-triazol-1-yl)-pentan-3-one (Example 5) were dissolved in 300 ml of methanol, and a solution of 13.2 g (0.35 mol) of sodium borohydride in 150 ml of 0.1 normal aqueous sodium hydroxide solution was added dropwise at 0° C. to 5° C. After a reaction time of 2 hours, the reaction solution was brought to a pH value of 4 to 5 with dilute aqueous hydrochloric acid. After addition of 500 ml of water, the end product crystallised out.

After drying in vacuo, 286 g (95% of theory) of 2,2-bisfluoromethyl-5-cyclohexyl-4-(1,2,4-triazol-1-yl)-pentan-3-ol of melting point 103° C. to 105° C. were obtained.

Comparison example

Preparation of the (1,2,4-triazol-1-yl) derivative of the formula

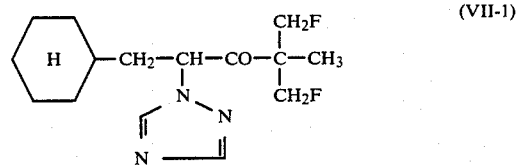

by the process known hitherto.

1st stage:

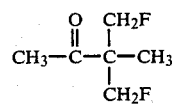

400 ml of tetraethylene glycol and 46.4 g of potassium fluoride (0.8 mol) were initially introduced into a three-necked flask with a stirrer, dropping funnel and a Liebig condenser with a cooled receiver, and were heated to 170° C. A water pump vacuum (pressure about 20 to 30 mbar) was applied to the adaptor of the Liebig condenser. 57.6 g (0.2 mol) of 2-acetyl-2-methyl-propane-1,3-diol bismethanesulphate, dissolved in 100 ml of tetraethylene glycol, were then added dropwise in the course of 45 minutes. The 3,3-bisfluoromethyl-butan-2-one formed was distilled off into the cooled receiver during the reaction. After the dropwise addition, the distillation was continued at 175° C. for a further hour. The distillate collected was then redistilled. 14 g (51.5% of theory) of 3,3-bisfluoromethylbutan-2-one of boiling point 43° to 46° C./12 mbar were obtained.

2nd stage:

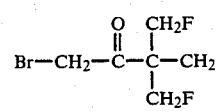

51 ml (1 mol) of bromine were added dropwise to 136 g (1 mol) of 3,3-bisfluoromethylbutane-2-one in 700 ml of methylene chloride such that decoloration was continuous. The solvent was then distilled off under a water pump vacuum. An almost quantitative yield of crude 3,3-bisfluoromethyl-1-bromo-butan-2-one was obtained as an oil, which could be further reacted directly.

3rd stage:

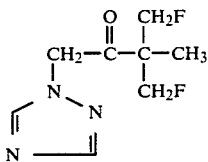

215 g (1 mol) of crude 3,3-bisfluoromethyl-1-bromobutan-2-one were added dropwise to 84 g (1.2 mol) of 1,2,4-triazole and 165 g (1.2 mol) of ground potassium carbonate in 1 liter of ethanol at 30° to 35° C. The mixture was subsequently stirred overnight at 40° C., the insoluble material was then filtered off and the filtrate was concentrated. The oily residue was extracted with methylene chloride and water and the extract was dried over sodium sulphate and concentrated. The residue was taken up in methylene chloride, and 140 ml of ethereal hydrochloric acid were added. The crystalline product formed was filtered off with suction and extracted with 1 liter of methylene chloride and 1 liter of saturated aqueous sodium bicarbonate solution, and the extract was washed with 1 liter of water, dried over sodium sulphate and concentrated. 73.8 g (36.4% of theory) of 3,3-bisfluoromethyl-1-(1,2,4-triazol-1-yl) were obtained as an oil, which could be further reacted directly.

4th stage:

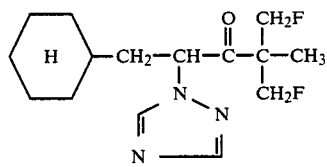

A solution of 101.4 g (1.81 mol) of potassium hydroxide into 7.2 ml of water was added to a solution of 369.4 g (1.81 mol) of 2,2-bisfluoromethyl-4-(1,2,4-triazol-1-yl)-butan-3-one in 2 liters of dimethylsulphoxide at room temperature, with stirring. 320.5 g (1.81 mol) of cyclohexylmethyl bromide were added dropwise to this mixture, with stirring, the temperature of the reaction mixture being kept between 20° and 40° C. by cooling. The reaction mixture was stirred at 60° C. for a further 15 hours and then poured into 2 liters of water. The resulting mixture was extracted twice with 1 liter of methylene chloride each time, the combined organic phases were washed four times with 2 liters of water each time and dried over sodium sulphate and the solvent was stripped off. The resulting oily product was taken up in acetone, and 326 g of naphthalene-1,5-disulphonic acid were added to the solution. The precipitate which thereby formed was filtered off with suction and suspended in 2 liters of methylene chloride. This suspension was shaken twice with 2 liters of saturated aqueous sodium bicarbonate solution each time. The organic phase was then washed with 2 liters of water and, after drying over sodium sulphate, was concentrated under reduced pressure. 297.5 g (63% of theory) of 2,2-bis-fluoromethyl-5-cyclohexyl-4-(1,2,4-triazol-1-yl)-pentan-3-one were obtained in this manner in the form of an oil. $n_D^{20} = 1.4837$.

It will be understood that the specification and examples are illustrative, but not limitative of the present invention and that other embodiments within the spirit and scope of the invention will suggest themselves to those skilled in the art.

What is claimed is:

1. A ketone of the formula

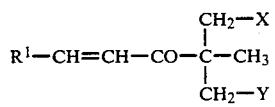

in which
R$^1$ is cycloalkyl with 5 to 7 carbon atoms, cycloalkyl with 5 to 7 carbon atoms which is mono-, di or tri-substituted by identical or different alkyl radicals with 1 to 3 carbon atoms, cycloalkenyl with 5 to 7 carbon atoms, cycloalkenyl with 5 to 7 carbon atoms which is mono-, di- or trisubstituted by identical or different alkyl radicals with 1 to 3 carbon atoms, phenyl, or phenyl which is mono-, di- or tri-substituted by identical or different alkyl radicals with 1 to 3 carbon atoms,
X is halogen and
Y is hydrogen or halogen.

2. A ketone according to claim 1, in which
X is fluorine or chlorine and
Y is hydrogen, fluorine or chlorine.

3. A ketone of the formula

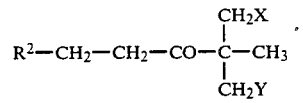

in which
R$^2$ is phenyl or phenyl which is mono-, di- or tri-substituted by identical or different alkyl radicals with 1 to 3 carbon atoms,
X is halogen and
Y is hydrogen or halogen.

4. A ketone according to claim 3,
in which
X is fluorine or chlorine and
Y is hydrogen, fluorine or chlorine.

* * * * *

UNITED STATES PATENT AND TRADEMARK OFFICE
CERTIFICATE OF CORRECTION

PATENT NO. : 4,661,640

DATED : April 28, 1987

INVENTOR(S) : Heinz Ziemann, et al.

It is certified that error appears in the above-identified patent and that said Letters Patent is hereby corrected as shown below:

| | |
|---|---|
| Abstract, Line 7 | After "halogen" delete "," and substitute --.-- |
| Col. 2, line 24 | Delete "(II)" and substitute --(I)-- |
| Col. 4, line 45 | Bottom of formula delete "$CH_2Y$" and substitute --$CH_2$-Y-- |
| Col. 6, line 33 | Delete "metal" and substitute --total-- |
| Col. 8, line 42 | After "0°C." insert --and 30°C.-- |
| Col. 9, line 61 | Delete "production" and substitute --product-- |
| Col. 12, line 51 | Delete "copper I" and substitute --copper-I-- |
| Col. 12, line 52 | After "10.6" delete "1" |
| Col. 14, line 57 | Right side of formula delete "$CH_2$" and substitute --$CH_3$-- |
| Col. 15, line 39 | Delete "7.2" and substitute --217.2-- |

Signed and Sealed this

First Day of December, 1987

Attest:

DONALD J. QUIGG

Attesting Officer       Commissioner of Patents and Trademarks